United States Patent [19]
Baker, Jr.

[11] Patent Number: 5,215,089
[45] Date of Patent: Jun. 1, 1993

[54] ELECTRODE ASSEMBLY FOR NERVE STIMULATION

[75] Inventor: Ross G. Baker, Jr., Houston, Tex.

[73] Assignee: Cyberonics, Inc., Webster, Tex.

[21] Appl. No.: 780,146

[22] Filed: Oct. 21, 1991

[51] Int. Cl.⁵ .......................... A61B 5/04; A61N 1/05
[52] U.S. Cl. ..................... 128/642; 128/784; 128/785
[58] Field of Search .................. 128/784, 785, 419 C, 128/642

[56] References Cited

U.S. PATENT DOCUMENTS

| | | | |
|---|---|---|---|
| 4,573,481 | 3/1986 | Bullara | 128/784 |
| 4,590,946 | 5/1986 | Loeb | 128/784 |
| 4,920,979 | 5/1990 | Bullara | 128/784 |
| 5,095,905 | 3/1992 | Klepinski | 128/784 X |

*Primary Examiner*—Lee S. Cohen
*Attorney, Agent, or Firm*—Leitner, Greene & Christensen

[57] ABSTRACT

A nerve electrode array includes one or more Y-shaped carriers in which the three legs of the Y are curled about a common axis with the lower leg of the Y oppositely directed relative to the other two so that the legs will encircle a nerve substantially sharing the common axis, and a flexible electrode secured to the underside of at least one of the legs.

9 Claims, 1 Drawing Sheet

ELECTRODE ASSEMBLY FOR NERVE STIMULATION

BACKGROUND OF THE INVENTION

The present invention relates generally to nerve electrodes, and more particularly to a claw-like electrode assembly or array which is implemented for ease of implantation on and electrical stimulation of a nerve of the patient.

U.S. Pat. No. 4,573,481 ("the '481 patent") discloses an implantable helical electrode assembly in which the configuration is composed of one or more flexible ribbon electrodes each partially embedded in a portion of the peripheral surface of a helically formed dielectric support matrix adapted to be threaded around a selected nerve or nerve bundle during surgical implantation of the electrode assembly. The resiliency of the assembly allows it to expand in the event of swelling of the nerve. The electrode assembly is utilized to electrically trigger or measure an action potential or to block conduction in nerve tissue.

Such a helical electrode has been found somewhat difficult to mount on the patient's nerve during implantation, because it is necessary to unravel the helical configuration and then reform it about the nerve. An improvement over the '481 patent electrode design is disclosed in U.S. Pat. No. 4,920,979 to the same inventor, in which a flexible electrode-supporting matrix has two oppositely directed helical portions which are centrally joined and have free outer ends. The helical portions extend circumferentially at least one turn and up to as much as about two turns. A thin, flexible conductive ribbon is secured to the inner surface to provide multiple electrodes on one or both portions, with a connecting electrical cable to couple the electrode array to an electronics package implanted elsewhere in the body.

The central passage through the two oppositely directed helical portions accommodates a pair of pins which extend at an acute angle from the respective closed legs of a tweezer-like installation tool. When the pins are inserted through the central passage and the legs of the tweezers are opened, the helical portions are distorted and spread open so that the assembly can be slipped over the nerve with the two open-sided portions restrained in a direction generally perpendicular to the length of the nerve. When released by withdrawing the pins of the installation tool, the two end portions return to a helical shape to encircle the nerve with their electrode portions conductively contacting the nerve surface. This type of electrode assembly simplifies installation of the electrode and reduces trauma to the nerve during implantation.

In U.S. patent application Ser. No. 07/695,543 filed May 3, 1991 ("the '543 application"), assigned to the same assignee as is the instant application, another improved helical nerve electrode or electrode array is disclosed. In this invention, the helix is locked together by a backbone which may be one-piece or divided into multiple segments. The electrode array is cut lengthwise through the entire helix at the side diametrically opposite to the backbone. The array is then spreadable at the cut ends of each loop, either one at a time or all together, and either manually or using an appropriate tool, to place it properly over the nerve. The array may then be allowed to collapse, as a consequence of its resiliency, into its unrestrained normal helical configuration about the nerve.

This provides the desirable features of a conventional helical electrode array, but with an improved configuration which allows it be opened in a manner similar to a clamshell when desired to install it on or remove it from the nerve. The array is relatively simple to install and unlikely to cause serious trauma to the nerve during or after implantation. In the latter respect, any subsequent swelling of the nerve is not restricted by the electrode. Some resistance to expansion may be experienced with a closed helical electrode array of the type described in the '481 patent, because of the tendency of the central portion of such a helix to resist expansion as the helix is subjected to outwardly directed radial forces.

In an alternative configuration of the electrode array of the '543 application, the cut in each loop or band of the helix is staggered relative to the cuts in the other bands to assure that the electrode array does not slip or otherwise become displaced from the nerve in the usual event of swelling of the nerve following the surgical implantation. Such swelling is likely to occur before stabilization, in the first few days following implantation of the electrode array. Fibrotic growth occurs and tends to retain everything in place after the first week to ten days following the surgery.

The nerve electrode array of the '543 application is made by forming an electrically insulative helix having a plurality of bands linked together by a lengthwise member, securing a electrically conductive strip to the underside of one of the bands and across the linking member, and severing each of the bands at a point away from the linking member so that each band remains linked to the member and may be spread open for mounting about the nerve.

It is a principal object of the present invention to provide an improved electrode or electrode array for nerve stimulation which is configured to permit relative ease of implantation and yet secure retention on a nerve compared to the prior art nerve electrodes.

Another object of the invention is to provide an improved nerve electrode which is simple to manufacture and simple to install without need for any special installation tool.

SUMMARY OF THE INVENTION

According to the present invention, a new and improved nerve electrode or electrode array for implantation on a patient's nerve includes a flexible electrically insulative carrier having a Y-shaped configuration with the three legs of the Y curled about a common axis, and a flexible electrode secured to the underside of at least one of the legs of the Y, so that the three legs will hold the electrode on a nerve which substantially shares the common axis therewith for stimulation of the nerve when the electrode is electrically energized. Electrically conductive lead means is electrically connected to the electrode to allow the electrode array to be energized by a stimulus generator.

In an electrode assembly or array, a second flexible electrically insulative carrier has a Y-shaped configuration with the three legs of the Y curled about the same axis but in the direction opposite that of the first-mentioned carrier, and has a flexible electrode secured to the underside of at least one of the legs of the Y of the second carrier. An electrically insulative spline parallel to the axis connects the first and second carriers together at opposite ends of the spline, and the electrically conductive lead means is also connected to the electrode of the second carrier to form a bipolar electrode array.

Therefore, yet another object of the invention is to provide an electrode array which is easier to install by virtue of the three pronged configuration of each claw of the array, which does not require any substantial force to spread nor create an awkward tendency of the assembly to twist.

A further object of the invention is to provide such an array in which each claw my be gently spread open during surgical implantation on the selected nerve of the patient, and, when released, has sufficiently resilience imparted by its cylindrical shaping formed during the curing stage of fabrication that each claw electrode of the array returns to its unrestrained curled shape to encircle the nerve.

BRIEF DESCRIPTION OF THE DRAWINGS

The above and still further objects, features and attendant advantages of the invention will become apparent from a consideration of the following detailed description of certain preferred embodiments thereof, taken in conjunction with the accompanying drawings, in which.

DETAILED DESCRIPTION OF THE PREFERRED EMBODIMENTS

Figure 1:
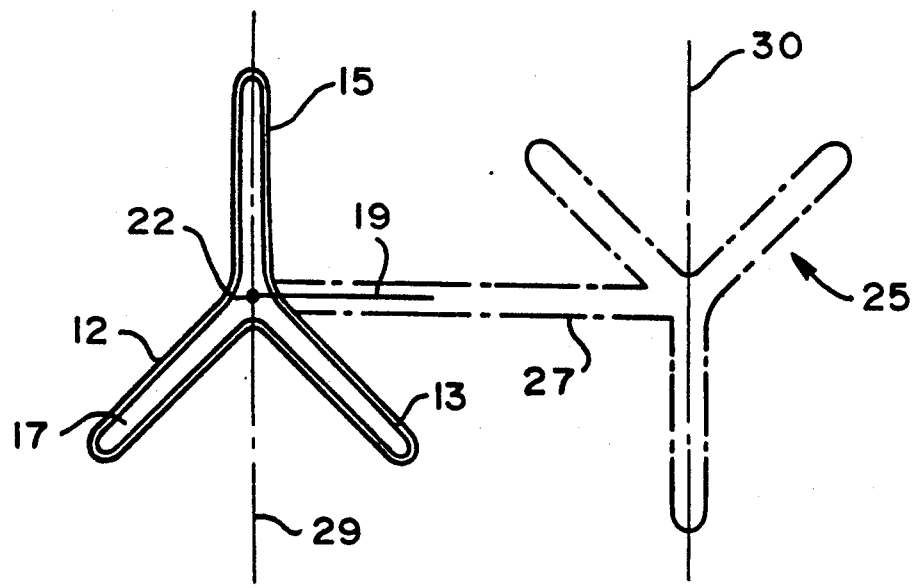
FIG. 1 is a flattened view of a preferred embodiment of a unipolar nerve electrode according to the invention, and in phantom, of a second corresponding electrode with connecting strip to form an electrode array for bipolar usage.

Referring to FIG. 1, a preferred embodiment of a nerve electrode 10 according to the invention has the shape of a bird's claw or a fork, with a V-shaped or U-shaped segment consisting of legs 12 and 13 and a spur-like segment 15 which produces an overall Y-shaped configuration. The claw is flexible and preferably composed of an electrically insulative medical grade silicone, available from Dow Corning, or other known biocompatible insulative material, to which barium sulfate has been added as a whitener to provide a sharp contrast between the electrode and the background as an aid in its installation on a nerve.

Figure 2:
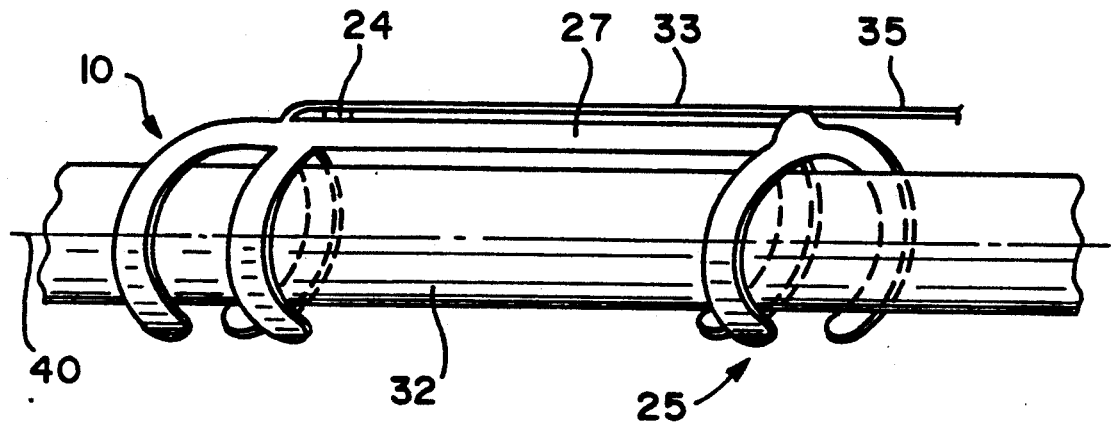
FIG. 2 is a perspective view of the nerve electrode array of FIG. 1 as implanted on a selected nerve of the patient.

Secured to the underside of at least one leg or spur of the claw, that is, to the side of the electrode which is intended to confront the nerve when installed thereon, is a flexible conductor 17. Preferably, the latter is an electrically conductive ribbon or foil which is likewise Y-shaped and is composed of iridium, although other known electrode materials such as rhodium or platinum may be used instead. Also, the conductor 17 may be a filament rather than a foil. Preferably, an iridium oxide coating is formed on the foil surface to improve the electrical characteristics of the electrode portion, including its sensitivity to electrical signals and its coupling to the nerve. The conductor, or electrode portion, is electrically connected, by welding or other conventional technique, at point 23 to the distal end of an electrically conductive lead which includes a filament or wire 19 within an insulative biocompatible sheath (such as 27 as shown in FIG. 2).

The claw electrode assembly described above is preferably fabricated by starting with a Y-shaped foil, and spot welding the lead connection to one side of the center junction of the Y. The other side of the foil is then covered with a water-soluble, high temperature double-sided adhesive tape having the same Y shape as the foil. The foil electrode is then applied, with the adhesive side down, to a conforming but slightly larger Y-shaped channel within a tubular mandrel. The foil is now retained at the bottom of the channel in the mandrel, and the medical grade silicone elastomer is then injected to fill the channel to form the insulative carrier over the foil. The mandrel is then rotated at high temperature to assure proper spreading of the elastomer to completely cover the foil beneath it in the channel. The assembly is then allowed to cool, and, after curing, the claw electrode is removed from the channel and the adhesive is removed by application of water to it.

The conductive element (foil) is thereby secured to the underside of the assembly along all (or, if desired, less than all) of the associated legs of the carrier. As a consequence of its manner of fabrication, the insulative carrier is resilient and, in its relaxed state, retains a cylindrical shape to cause the electrode assembly to curl naturally about the nerve. Each of the conductors and leads may be covered with a respective thin insulative sheath of biocompatible material to prevent penetration of body fluids.

The lead may be further secured to the silicone carrier by a tether (e.g., 24 as shown on FIG. 2) which may be simply a short span of silicone. A tether provides greater protection against lead breakage by stresses encountered during and after the electrode assembly is implanted. To improve such protection in the acute phase, but provide greater flexibility and ultimate retention by fibrotic growth about the lead, the tether may be instead be formed from known biocompatible material which is absorbed (e.g., dissolved by the body fluid) within a relatively short period of time.

The proximal end of each lead may be electrically connected to an electrical connector designed to mate with the electrical connector of an implanted generator (not shown) of electrical signals for electrical stimulation of the nerve and/or of a detector (not shown) for use in sensing the electrical signals carried by the nerve.

The nerve electrode assembly may be unipolar or bipolar. Referring to FIGS. 1 and 2, a bipolar electrode array includes a second claw or fork 25 which is linked to the first claw 10 by an electrically insulative (e.g., medical grade silicone) spline 27, shown in the added phantom portion of FIG. 1. Claws 10 and 25 are attached to (actually, formed together with) the spline 27, with their respective axes of symmetry 29, 30 generally perpendicular to the spline an their Y-configurations in opposite directions to each other. Preferably, the spline is somewhat more rigid than the claw at either end thereof, to assure that the assembly is not overly limp which might otherwise create difficulty during the implant procedure.

FIG. 2 illustrates the dual claw bipolar electrode array or assembly installed over a nerve 32. No conductive foil is secured to or embedded as an electrode portion to the underside of spline 27 but the electrical lead portion 33 is conveniently carried on or secured adjacent to the spline, with the overall lead 35 having conductive filaments connected to the respective electrode foil portions of the two claws.

Whether a bipolar or a unilpolar electrode assembly is implanted on the nerve, the array operates in a conventional manner to produce electrical stimulation of the nerve 32 by application of stimulating signals to the lead from a stimulus generator (not shown).

Thus, it will be seen that a single electrode for implantation on the nerve of a patient includes a resilient electrically insulative portion in the form of a first leg 15 having a longitudinal axis of symmetry 29 and second and third legs 12 and 13 connected to the first leg at one end thereof and extending from the connection at opposite sides of the axis of symmetry in a direction substantially opposite to the direction of the first leg. The insulative portion has a cylindrical configuration in the relaxed state with an axis 40 normal to the axis of symmetry 29, so that the three legs will at least partly encircle the nerve 32 from opposite directions for retention thereabout after implantation. The electrically conductive portion of the electrode is secured to the inside surface of at least one of the legs in the cylindrical configuration for electrical interaction with the nerve.

In the preferred embodiment, the second and third legs diverge from each other at the connection with the first leg and on opposite sides of the axis of symmetry. The insulative portion is composed of substantially flat material, and the conductive portion is a foil secured to the side of the material closest to the axis of the cylinder. An electrical lead is connected to the foil to carry electrical signals to or from the foil, to or from the nerve on which the electrode is implanted.

An electrode array has an electrically insulative strip 27 connected at one end to the juncture of the three legs of the insulative portion of electrode 10 and extending therefrom parallel to the axis of the cylinder, so that the strip and the cylinder axis lie in the same plane. Another electrode 25 substantially identical to the electrode 10 is connected at the other end of the strip 27 to the juncture of the three legs and normal to the axis of symmetry of electrode 25, with its corresponding first leg extending from the juncture in a direction opposite to that of the first leg 15 of electrode 10. The two electrodes at opposite ends of strip 27 are connected to the strip so that when they are constrained to be entirely flat, both electrodes are in the plane of the strip. Another lead is electrically connected to the foil of electrode 25.

In practice, the nerve electrode assembly or array constructed and configured according to the present invention is more easily installed on and retained about the nerve than the prior art configurations such as those described in the background section above. Easier installation is attained because the three pronged configuration of each claw does not require any substantial force to spread nor create an awkward tendency of the assembly to twist, as occurs with a helical shaped electrode of one or more turns. Each claw of the assembly is gently spread open during surgical implantation on the selected nerve of the patient, such as the vagus nerve. When released, the resilience of the cylindrical shaping formed during the curing stage of its fabrication causes the claw electrode to return to its unrestrained curled shape to encircle the nerve.

After the nerve electrode has been installed, it is securely retained on the nerve because each claw of the array is held at three points, i.e., the two legs of the V-shaped member and the oppositely directed spur, as the electrode curls about the nerve in its unrestrained state. Furthermore, adequate expansion is available without unseating or creating pressure on the nerve which could occlude a blood vessel.

It will be appreciated that the nerve electrode assembly constructed according to the principles of the present invention provides a superior configuration in that it retains the desirable elctrical and mechanical features of the helical configuration, while being adapted for ease of mounting the assembly on the nerve itself, thereby significantly reducing the likelihood of trauma to the nerve during the installation. The electrode array is neither a complete loop or band, nor a spiral or a helix.

Although certain presently preferred embodiments and methods of making such embodiments of the invention have been described herein, it will be apparent to those skilled in the field to which the invention pertains from a consideration of the foregoing description, that variations and modifications of the disclosed embodiments and methods may be made without departing from the spirit and scope of the invention. It is therefore intended that the invention shall be limited only to the extent required by the appended claims and the rules and principles of applicable law.

What is claimed is:

1. An electrode array for implantation on a patient's nerve, comprising:
    first and second means for retention on the nerve, each retention means including
        a flexible electrically insulative carrier having a Y-shaped configuration with the three legs of the Y stemming from a common juncture and curled about a common axis, and
        a flexible electrode secured to the underside of at least one of the legs of the Y, whereby the three legs hold the electrode on a nerve which substantially shares the common axis for stimulation of the nerve when the electrode is electrically energized; and
    an elongate strip connecting the first and second retention means at the respective common junctures thereof at opposite ends of the strip, with the Y-shaped configurations oppositely directed from the strip substantially normal thereto about said common axis and separated from each other solely by the connecting strip and empty space.

2. The invention of claim 1, further including
    at least one electrically conductive lead electrically connected to said electrode of one of said first and second retention means and running along said strip.

3. The invention of claim 2, wherein
    a second electrically conductive lead is electrically connected to the electrode of the other of the first and second retention means to form a bipolar electrode array.

4. An electrode assembly for implantation on a nerve of a patient, comprising
    resilient electrically insulative means for retaining the electrode assembly on the nerve, in the form of a first leg having a longitudinal axis of symmetry and second and third legs connected to said first leg at one end thereof and extending from the connection at opposite sides of said axis of symmetry in a direction substantially opposite to the direction of the first leg, said second and third legs diverging from each other at said connection on opposite sides of said axis of symmetry,
    said insulative means having a cylindrical configuration in a relaxed state with inside and outside surfaces and an axis normal to said axis of symmetry, so that the three legs will at least partly encircle the nerve from opposite directions for retention thereabout after implantation, and electrically conductive means secured to at least one of the legs at the inside surface of the cylindrical configuration as an electrode for electrical interaction with the nerve.

5. The invention of claim 4, wherein
said insulative means is substantially flat material, and
said electrically conductive means is a foil secured to said inside surface of the cylindrical configuration.

6. The invention of claim 5, further including
an electrical lead connected to said foil to carry electrical signals to or from said foil, to or from the nerve on which the electrode assembly is implanted.

7. The invention of claim 6, further including
an electrically insulative strip connected at one end to said connection of the first, second and third legs of the insulative means and extending therefrom parallel to the axis of the cylindrical configuration, so that the strip and the cylindrical configuration axis lie in the same plane;
a second resilient electrically insulative means for retaining the electrode assembly on the nerve, said second resilient electrically insulative means having the form of three legs with a common connection and a cylindrical configuration substantially identical to the first mentioned resilient electrically insulative means and connected at the other end of the strip to the connection of the three legs and normal to the axis of symmetry of the second resilient electrically insulative means, with the first leg of the second resilient electrically insulative means extending from the connection of the three legs thereof in a direction opposite to that of the first leg of the first resilient electrically insulative means;
said second resilient electrically insulative means having a foil electrode secured to an inside surface of the cylindrical configuration thereof; and
a second electrical lead electrically connected to the foil electrode of the second resilient electrically insulative means.

8. An electrode assembly for installation on a patient's nerve for electrical interaction therewith, comprising
first and second Y-shaped resilient electrical insulators fastened at the center of the respective Y to opposite ends and in the plane of an elongate electrically insulative connecting strip with the base leg of the Y of one insulator projecting in a direction opposite that of the base leg of the other insulator substantially perpendicular to the orientation of the strip, each of said insulators having a normal relaxed state in which the three legs of the Y are curled about a longitudinal axis of the assembly parallel to the orientation of the strip, and each insulator having an electrical conductor integral therewith and spaced from the insulator at the opposite end of the strip with no other intervening structure therebetween.

9. The electrode assembly of claim 8, further including separate electrically conductive leads connected to respective ones of the electrical conductors associated with the two Y-shaped insulators.

* * * * *